United States Patent [19]

Woog

[11] 4,195,329
[45] Mar. 25, 1980

[54] DIAGNOSTIC LAMP, PARTICULARLY FOR CHECKING TEETH

[75] Inventor: Philippe-Guy E. Woog, Vesenaz, Switzerland

[73] Assignee: Les Produits Associes LPA SA, Geneva, Switzerland

[21] Appl. No.: 856,396

[22] Filed: Dec. 1, 1977

Related U.S. Application Data

[63] Continuation-in-part of Ser. No. 744,751, Nov. 24, 1976.

[30] Foreign Application Priority Data

Jun. 8, 1977 [DE] Fed. Rep. of Germany ....... 2725793

[51] Int. Cl.² .............................................. B25B 23/18
[52] U.S. Cl. .................................. 362/120; 362/155; 362/206; 362/253; 362/804
[58] Field of Search ............... 42/1 A, 1 G; 362/109, 362/119, 120, 155, 189, 196, 202–206, 253, 804

[56] References Cited

U.S. PATENT DOCUMENTS

| | | | |
|---|---|---|---|
| 1,461,600 | 7/1923 | Cottrell | 42/1 A |
| 1,647,862 | 11/1927 | Galliard | 32/69 X |
| 2,393,319 | 1/1946 | Freedman | 362/804 X |
| 2,565,895 | 8/1951 | Wadland | 362/155 |
| 2,618,736 | 11/1952 | Langhout | 362/155 X |
| 2,625,764 | 1/1953 | O'Brien et al. | 42/1 G |
| 2,885,537 | 5/1959 | Wood, Jr. | 362/119 |
| 3,619,930 | 11/1971 | Beermann et al. | 42/1 G |
| 3,704,928 | 12/1972 | Coombs et al. | 362/804 X |
| 3,710,092 | 1/1973 | Olbermann, Jr. | 362/205 |
| 3,812,847 | 5/1974 | Moore et al. | 362/253 X |

*Primary Examiner*—Peter A. Nelson

[57] ABSTRACT

A diagnostic lamp for fluorescent excitation of a fluorescible material applied to parts of the body, and particularly useful for preventive checking of the teeth and gums by self-observation. A housing is provided with a light source and battery for supplying power thereto, a dispenser for fluorescible material, and a mounting structure for coupling the dispenser to the housing in a manner permitting its replacement. The dispenser is arranged on a first insert assembly. The batteries, lampholder and bulb, switch and leads are mounted on a second insert assembly, and the assemblies can be pushed into either open end of the housing and locked into position.

7 Claims, 8 Drawing Figures

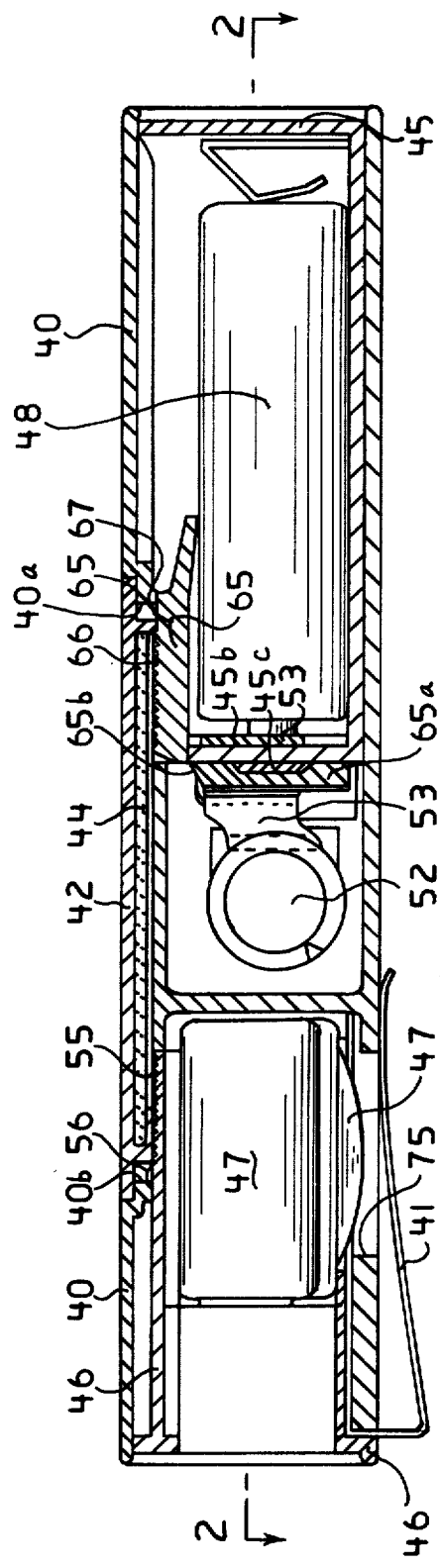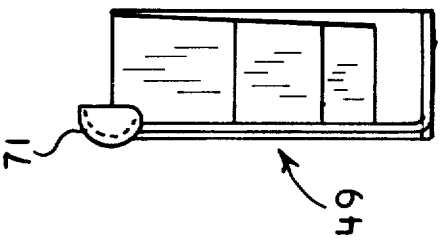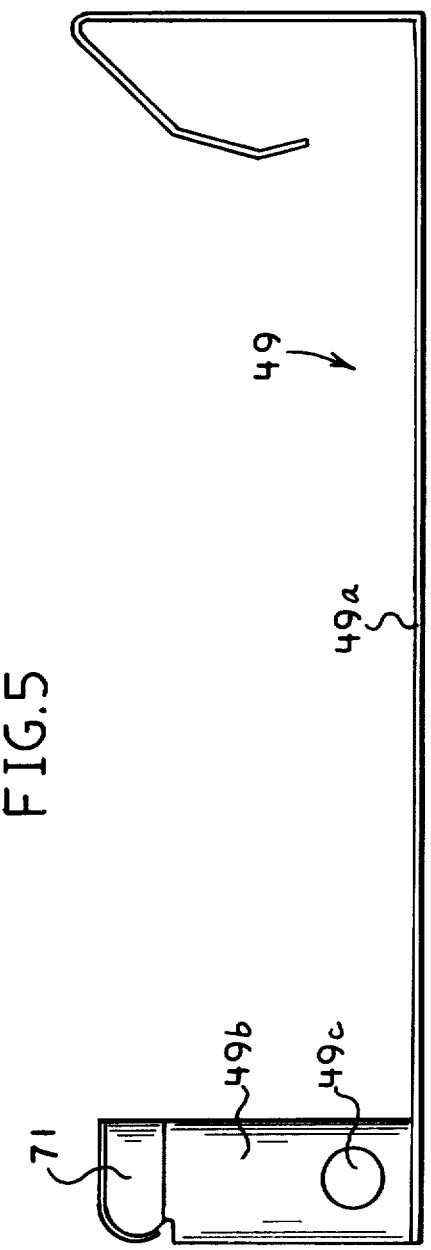

DIAGNOSTIC LAMP, PARTICULARLY FOR CHECKING TEETH

CROSS-REFERENCE TO RELATED APPLICATION

This application is a continuation-in-part of Ser. No. 744,751 filed Nov. 24, 1976.

BACKGROUND OF THE INVENTION

The present invention relates to a diagnostic lamp for fluorescent excitation of a fluorescible material applied to a part of the body to be tested, for example the teeth and gums.

In dental therapy, it is known and customarily the practice to make plaque easily distinguishable by painting a fluorescible solution on the teeth and then exciting it to fluorescent radiation by means of suitable lamps. Plaque is the coating on the teeth which consists mainly of bacteria and causes disease of the teeth and gums, and normally is invisible. It has been shown that fluorescible material only or at least preferably remains adhered to the plaque, but not to the clean and healthy teeth and parts of the teeth. The same goes for those parts on which tartar has formed by mineralization of the plaque or which already have been attacked by dental decay. Thus, these critical or respectively diseased parts of the teeth may in a simple manner be made visible and located by the foregoing checking treatment and procedure, since only these parts fluoresce under illumination and hence are brought into sharp relief against the other non-fluorescent regions. In addition, by the fluorescent effect, diseased places on the gums as well as other diseased regions of skin and tissue can also be made visible.

A test lamp has been proposed for the purpose described and utilizes an incandescent lamp as light source, together with a dichroic reflector behind the lamp and a dichroic filter in front of the lamp as well as preferably another dichroic observation mirror which has the same transmission and reflection characteristics as the filter. In that way the radiation available for illumination of the parts to be tested is restricted essentially to blue light which particularly excites a fluorescein solution; and, as far as possible, only a little radiation is emitted having those wave lengths which correspond with the color of the yellow or green fluorescent radiation. Only in this manner can a significant contrast be achieved between the fluorescing regions and their non-fluorescing surroundings. Otherwise the non-fluorescing surroundings under illumination with the light of the fluorescent radiation would appear approximately of the same hue as the latter.

This known test-lamp is costly to produce and consequently is relatively expensive. It is complicated in construction and also troublesome to handle. Furthermore, the user must always be concerned that the fluorescent material too, which is indispensable and normally in liquid form, is always handily available. For these reasons the test-lamp does not fulfill those prerequisites which would favor an otherwise wide distribution amongst the consuming public interested in oral hygiene and regular self-checking of the condition of the mouth, particularly the teeth and gums.

SUMMARY OF THE INVENTION

An object of the present invention is to provide a diagnostic lamp which is simply constructed and can be produced inexpensively, yet which can be handled easily and conveniently by the user, and hence can be used for preventive checking of teeth by regular self-observation.

According to the present invention there is provided a diagnostic lamp for fluorescent excitation of a fluorescible material applied to a part of a body to be tested, comprising a housing having two opposing open ends, a light source and means for supplying electrical energy to the light source mounted on a first insert assembly, and a dispenser for the fluorescible material, mounted on a second inert assembly. The insert assemblies are pushed into one or the other open ends of the housing prior to use of the device.

It has been found that a comparatively simply constructed pocket-lamp is adequate, the light from which exhibits wave lengths shorter than those of the fluorescent radiation to be excited. In addition, the light does not for all practical purposes, or to such a slight degree, contain the color of the spectral range of this fluorescent radiation. Thus, there is more than adequate contrast between the excited fluorescent light and the non-fluorescing surroundings illuminated by the lamp. For that purpose, it is of particular significance that it is sufficient to equip the pocket lamp with a normal incandescent lamp of adequate brightness and with a filter adapted to the fluorescent material to be employed in such a way that the exciting radiation necessary to the generation of the fluorescence is transmitted in adequate strength and the spectral range of the fluorescent radiation itself is adequately absorbed. Thus, in the case of the employment of, for example, fluorescein as the fluorescible solution which emits green fluorescent light, just one filter may be employed which essentially absorbs green light and adequately transmits blue light. If eosin is employed as the solution the filter must essentially transmit the exciting green light and absorb in the yellow-orange range of the emitted fluorescent radiation. The filter may also be simply the correspondingly colored incandescent bulb itself.

In order to permit self-checking of the teeth by the diagnostic lamp of this invention, a mirror may be attached to the housing of the pocket lamp. This mirror may be collapsed inwardly when not in use and folded outwardly to its operating position at which, upon illuminating the teeth with the pocket lamp, permits the user observation of his teeth directly.

The exchangeable dispenser is arranged on a first insert assembly, and a complete electrical installation with batteries, lampholder and bulb, switch and leads is mounted on a second insert assembly, which can be pushed into one or other of the open ends of a casing and locked in position by catches. The mirror is secured to the inside of a hinged cover, which operates in conjunction with the switch in such a way that when the cover is closed, the lamp is switched off, and switched on again automatically when the cover is open. The dispenser preferably comprises a container of flexible plastic material, and is provided with an outlet connection, to which is attached a hinged discharge pipe, which in a retracted position, shuts off the outlet connection, and in a swung-out position, is lined up with same. Fluid can then be easily sprayed from the discharge pipe by the application of pressure to a portion of the dispenser wall which is accessible from the exterior thereof.

The present invention will now be described by way of example with reference to the accompanying drawings, in which:

BRIEF DESCRIPTION OF THE DRAWINGS

FIG. 1 is a longitudinal section view of an embodiment of a lamp according to the present invention;

FIGS. 5 and 6 are side and end views of a contact strip of the lamp; and

Figure 2:
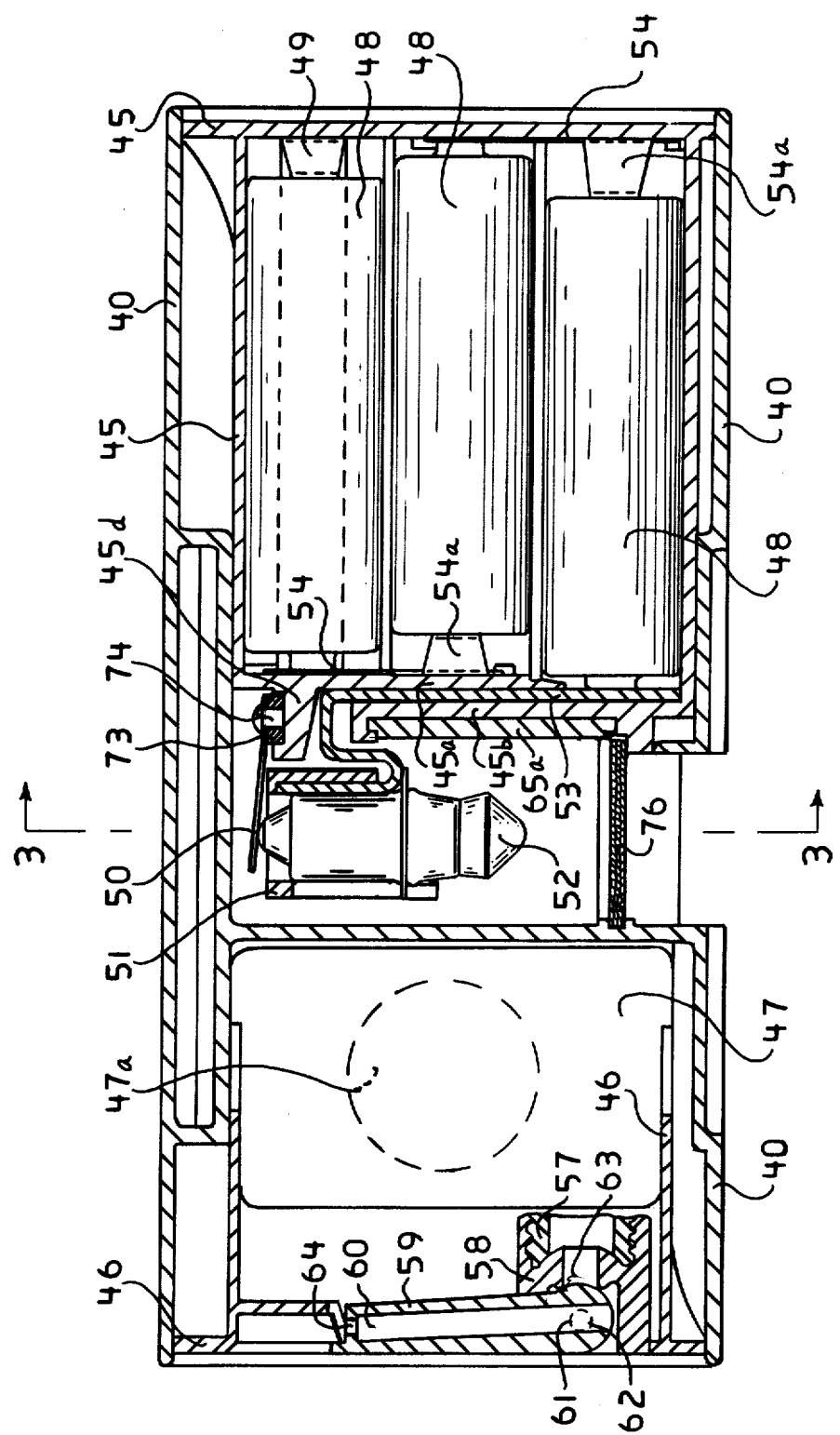
FIG. 2 is a section along the line II—II of FIG. 1.

The diagnostic lamp is shown in FIGS. 1-8, and comprises a flat, elongated housing 40 with fastening clip 41 (FIG. 1) fitted at one end and a cover 42 provided in its center section and including an insert assembly 45 which carries the batteries 48 together with the other electrical components, and which is inserted in one end of the housing, and an insert assembly 46 for the dispenser 47, which is inserted into the other end of the housing. The cover 42, to the inside of which a mirror 44—preferably concave—is fixed is flexibly secured to the housing 40 by means of a pliable plastic component 43 (FIG. 3), which is attached to the inner surface of one longitudinal side of the housing, and which acts as a hinge.

The insert assembly 45 is provided on its inner face with two spaced wall sections 45a and 45b (FIG. 2) and between which is clamped a metallic contact spring 53, which is in contact with one pole of the lower of batteries 48 in FIG. 2. The contact spring 53 is bent approximately into an S-shape outside the wall sections 45a and 45b and its free end provides a contact within the lampholder 51 for the lamp-bulb 52 located approximately in the center beneath the cover 42. At the back, on the wall section 45b of the insert 45 adjoining the lamp-bulb 52 and secured between suitable lateral projections on this wall section, is a fastening plate 65a of a locking piece 65 (FIG. 1), which is connected to the fastening plate 65a through a flexible area 65b of reduced wall thickness, and which is bent at this point at right-angles to the fastening plate 65a. A circular projection 45c formed on the wall section 45b engages the fastening plate 65a in a mating recess for centering purposes. On the upper side of the locking piece 65 is a corrugation 66, which is accessible on opening the cover 42, and a projection 67 serving as a hook, which, in the inserted position of the assembly 45 as shown in FIG. 1, locks this against a joint edge 40a of the housing 40. In order to withdraw the insert assembly 45 complete with batteries 48 and the lampholder 51 with lamp-bulb 52, it is only necessary for the locking piece 65 to be bent inwards by light pressure on the corrugation 66 until the projection 67 can slide beneath the joint edge 40a.

Figure 3:
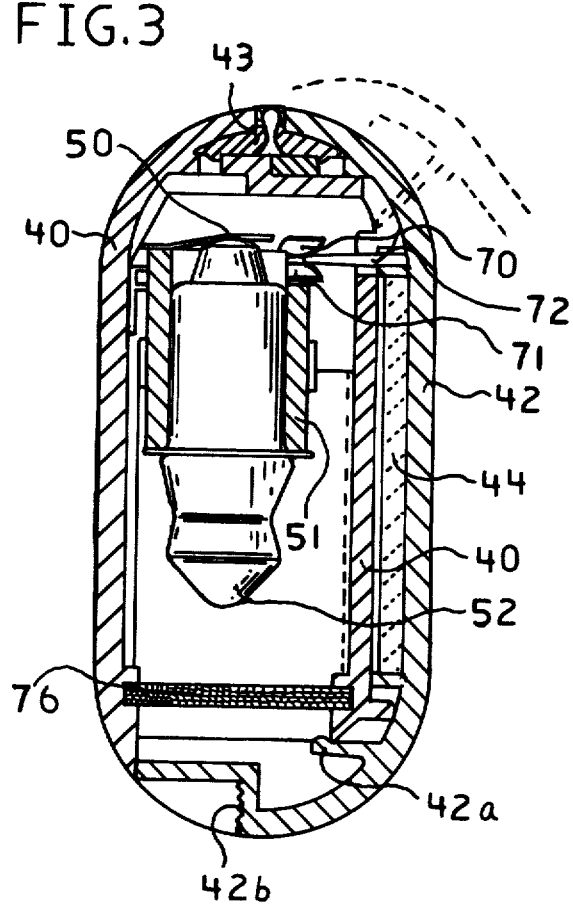
FIG. 3 is a section along the line III—III of FIG. 2, with a cover of the lamp closed.
Figure 4:
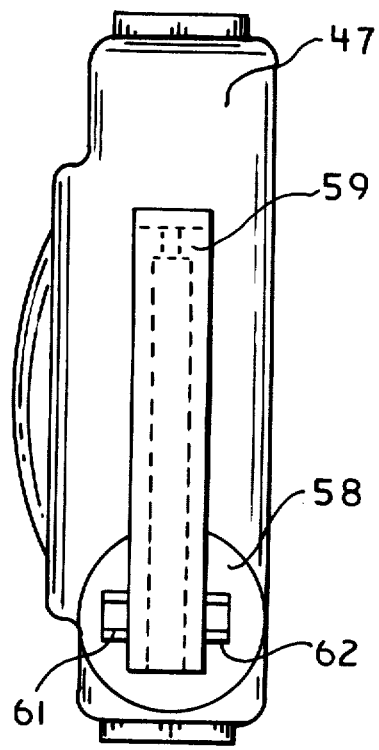
FIG. 4 is a front view of a dispenser of the lamp with its retracted discharge pipe.
Figure 7:
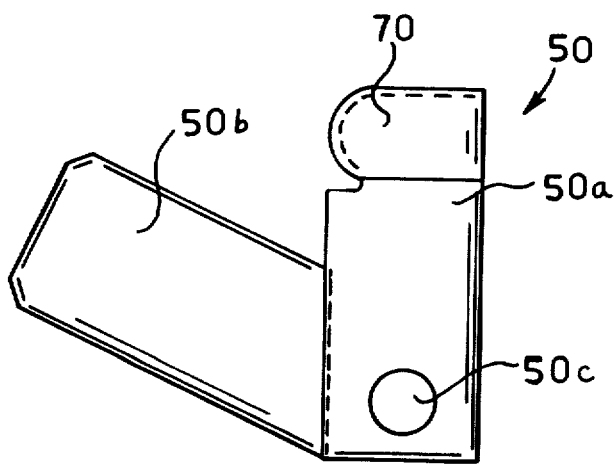
FIGS. 7 and 8 are side and end views of a second contact strip of the lamp.
Figure 8:
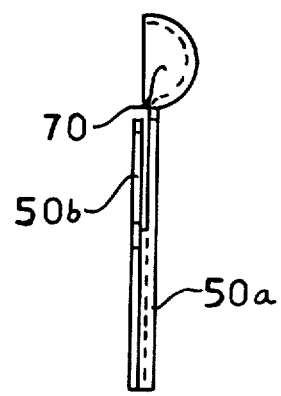

In the example under consideration, the insert assembly 45 contains the three batteries 48 (FIG. 2), which are connected in series and held in position in the usual way by an electrical conductor 54 with spring tongues 54a. The right-hand pole in FIG. 2 of the upper battery 48 is in contact with a contact strip 49, which is depicted in two views in FIGS. 5 and 6, and which consist essentially of a strip 49a running along the battery and a section 49b bent at right-angles at the inner end. This section 49b which points in the direction of the cover 42 and is located in the vicinity of the hinge 43, is provided with an opening 49c, and at the free end forms a spring contact 71, which is spherically curved in the areas turned away from the hinge 43 and towards the cover 42 (FIG. 3). Opposite to this section of the spring contact 71, is also a mirror-image spherically curved section of a spring contact 70, which is formed on the end of a further contact strip 50. The form of this contact strip 50 is depicted in two views in FIGS. 7 and 8, and shows two sections 50a and 50b at an angle to one another, in which the section 50a forming the spring contact 70 is provided with an opening 50c, while the other section 50b forms the spring contact for the rear end of the lamp-bulb 52 (FIG. 2). Both the contact strips 49 and 50 are secured and electrically insulated from one another on an internal projection 45d of the insert assembly 45, and with the interposing of an insulating piece 73, by means of a pin 74 of non-conducting material which passes through the openings 49c and 50c, arranged in such a way that their spring contacts 70 and 71 are forced apart by a wedge-shaped projection 72 on the cover when the latter is closed, so that the circuit to the lampbulb 52 is broken.

In FIG. 3, the switch formed by the two spring contacts 70 and 71, is shown in its closed position, in which the projection 72 is forced between the two contacts. The cover 42 is retained in its closed position by a flexible stop 42a, which grips the back of an edge of the casing. When the cover 42 is opened, whereby the projection 72 is withdrawn from between the two spring contacts 70 and 71, the latter come into contact due to their elasticity, and so close the circuit for the lamp-bulb 52. The partially opened cover is shown in dotted outline in FIG. 3. A corrugated section 42b of a stepped portion of the cover facilitates the pressing on of the cover 42.

A filter 76, preferably of a dichroic type, is inserted in the casing in front of the lamp-bulb 52. The other insert assembly 46 for the dispenser, is also provided on its upper side with a locking piece with corrugations 55 and a hook-shaped projection 56, which locks the assembly 46 in the inserted position (FIG. 1) to a joint edge 40b of the housing 40. The insert assembly 46 may be unlocked by pressure on the corrugated section 55 which is accessible when the cover 42 is open, and then readily withdrawable from the housing 40.

The dispenser 47 consists of a container of roughly square section, composed of a flexible plastic material, and is provided with an outlet connection 57 (FIG. 2), on to which is screwed a sleeve 58, carrying a swivelling discharge pipe 59. The pivoting end of the discharge pipe 59 carries two formed hinge pins 61, which are inserted free to rotate in suitable recesses 62 in the sleeve 58, preferably in the form of a positive locking arrangement.

In the retracted rest position of the discharge pipe 59 shown in FIG. 2, in which it drops into a recess in the face of the casing and the insert assembly 46, the internal aperture 63 of the sleeve 58, and thereby the outlet connection 57 of the dispenser 47, is closed by the side face of the pivoted end of the discharge pipe 59. In order to utilize the dispenser, the discharge pipe 59 is swung out by 90° in an anti-clockwise direction (opposite to the direction as shown in FIG. 2), so that the internal passage 60 of the discharge pipe 59, terminating in the discharge opening 64, now lines up with the sleeve 58 and the outlet connection 57. In order to spray fluid from the dispenser 47 through the discharge pipe 59, it is only necessary for the user to press the dished area 47a of the dispenser 47, which is accessible through a suitable opening 75 in the underside of the housing 40 (FIG. 1). Afterwards, the discharge pipe 59 is swung back again into the retracted position, whereby the dispenser 47 is shut off.

In order to undertake the examination of teeth, it is then only necessary to open the cover 42, whereby, as previously, described, the lamp-bulb 52 is put in circuit, when the teeth, illuminated by the filtered light, can be readily examined in the mirror 44. On the completion of the examination, the cover 42 is re-closed, whereby the lamp-bulb 52 is extinguished, the closed cover at the same time providing protection for the filter 76.

In a modification, the housing 40 may be formed in two parts, whereby one section represents, or accommodates, the dispenser, and can be attached to the other lamp section containing the battery and lamp-bulb, by means of a flexible collar for example. The constructional form can also be such that after opening the cover, which can also extend for the full length of the housing, batteries and dispenser can be inserted directly into the housing.

What is claimed is:

1. A diagnostic lamp for fluorescent excitation of a fluorescible material applied to a part of a body to be tested, comprising:
    a housing of a size which can be handled easily and conveniently by a user, said housing having two opposing open ends;
    two insert assemblies, each of which is removably push fitted into one of the two opposing open ends of said housing;
    one of said insert assemblies including a light source and adapted for accommodating a power supply for said light source, and associated electrical circuitry;
    the other of said insert assemblies containing a dispenser for fluorescible material;
    a filter positioned in-front of said light source for allowing the transmission of a exciting radiation necessary to the generation of fluorescence of the fluorescible material; and
    a cover attached to the housing, having a mirror on an inside surface thereof, said cover being movable between an open position where the light source and mirror are exposed and a closed position in which the light source and mirror are protected by said cover.

2. A diagnostic lamp as claimed in claim 1, wherein an electrical switch is provided for the light source and comprises two flexible spring contacts urged apart by an electrically insulated projection on the innermost surface of a cover forming a part of the housing when this cover is in a closed position, opening of the cover causing the projection to release the spring contacts which then can make contact to close the electrical circuit including the light source.

3. A diagnostic lamp as claimed in claim 2, wherein the insert assemblies can only be unlocked from the housing when the cover is in an open position.

4. A diagnostic lamp as claimed in claim 1, wherein the dispenser comprises a flexible container with an outlet connection to which is attached a discharge pipe movable between a retracted position, in which the face of the pipe closes the outlet from the container, and an extended position, in which the pipe is aligned with the outlet connection, means being provided to compress the wall of the flexible container to excude fluid therefrom through the discharge pipe.

5. A diagnostic lamp as claimed in claim 4, wherein a part of the wall of the flexible container is accessible through an opening in the housing to permit manual compression thereof.

6. A diagnostic lamp as described in claim 1 wherein each of said insert assemblies includes locking pieces having projections and upper sides provided with corrugations, said housing having edges against which the projections lock when the insert assemblies are in an inserted position, the insert assemblies and said projections capable of being unlocked when pressure is exerted by a user on said corrugations only when said cover is an open position.

7. A diagnostic lamp as described in claim 1 further including in combination at least one battery within said one insert.

* * * * *